US005489260A

United States Patent [19]

Striano

[11] Patent Number: 5,489,260
[45] Date of Patent: Feb. 6, 1996

[54] LUMBAR SPINE SUPPORT

[76] Inventor: James S. Striano, 475 Tuckahoe Rd., Ste. 201, Yonkers, N.Y. 10710

[21] Appl. No.: 326,699

[22] Filed: Oct. 20, 1994

[51] Int. Cl.⁶ ........................................ A61F 5/00
[52] U.S. Cl. ................. 602/19; 2/44; 2/311; 2/322; 2/325; 128/96.1; 128/100.1; 128/106.1; 128/107.1
[58] Field of Search ................... 602/19; 2/300, 2/310, 311, 317, 255, 319, 235–237; 128/96.1, 100.1, 101.1, 106.1, 107.1

[56] References Cited

U.S. PATENT DOCUMENTS

| | | | |
|---|---|---|---|
| 2,541,487 | 12/1949 | Triplett . | |
| 2,828,737 | 4/1953 | Hale . | |
| 4,475,543 | 10/1984 | Brooks et al. | 602/19 |
| 5,046,488 | 9/1991 | Schiek, Sr. | 602/19 |
| 5,179,942 | 1/1993 | Drulias et al. . | |
| 5,207,636 | 5/1993 | Striano | 602/19 |
| 5,267,947 | 12/1993 | James et al. | 602/19 |
| 5,310,401 | 5/1994 | Striano | 602/19 |
| 5,384,134 | 8/1994 | Saunders | 602/19 |

Primary Examiner—Richard J. Apley
Assistant Examiner—Kim M. Lee
Attorney, Agent, or Firm—Charles J. Prescott

[57] ABSTRACT

An improved lumbar spine support including a posterior shell form-fitted around the corresponding torso area. This shell is connectable by flexible fabric support belt arrangement tightly against the torso. The posterior shell includes an elongated upright indentation having a laterally extending wider lower portion for centering and securing the posterior shell over the lumbosacral area of the spine. A tightening strap arrangement connected to the support belt provides increased independent right and left side tightening of the posterior shell against the torso.

7 Claims, 2 Drawing Sheets 5,489,260

LUMBAR SPINE SUPPORT

BACKGROUND OF THE INVENTION

1. Scope of Invention

This invention relates generally to body torso supports, and more particularly to a semi or substantially rigid orthosis which provides unique lumbar centering and abdominal lifting features.

2. Prior Art

Devices in the form of rigid, semi-rigid, or flexible material constructed to at least partially surround the lower back region of the human torso are well-known for the treatment and rehabilitation of spinal disfunction. One such device is shown in U.S. Pat. No. 4,508,110 to Modglin which discloses a body jacket constructed in two parts to be laced together into a final adjusted position and then easily installed and removed thereafter.

Another device known to applicant is shown in U.S. Pat. No. 4,696,291 invented by Tyo directed to a device for treating lower back pain comprising three generally rigid members which, when properly installed, are claimed to apply a centrally directed beneficial force to the abdomen and the gluteal muscles.

Rowe in U.S. Pat. No. 4,930,499 teaches a sacral brace intended for comfortable extended wear including a rigid posterior sacral pad having a vertical central channel and connectable to an abdominal leverage plate provided for anchoring the sacral pad by tying straps.

A simple brace and method of application is disclosed in U.S. Pat. No. 5,074,292 to Cox for immobilization of various regions of the torso.

The Triplett U.S. Pat. No. 2,541,487 discloses a spinal brace including a main metal frame having a pair of upright bars which are co-extensive and spaced apart to define an open central area positionable along the spine of the user.

The present invention provides a lumbar spine support comprised of a posterior shell or section vertically symmetrical, horizontally asymmetrical in nature to accommodate the bony prominences known as the anterior superior lilac spine (ASIS), the lilac crest and the lumbosacral spine. The posterior shell includes an upright indentation with an oblong shaped transverse bottom portion conforming to the skeletal cavity created at the junction of the lumbar vertebra and the sacrum serving to guide the placement of the posterior shell to insure centering over the spine and locking onto the lumbosacral area to facilitate appropriate dispersion of the lower abdominal resistive force when the adjustable closure system is tightened.

BRIEF SUMMARY OF THE INVENTION

This invention is directed to an improved lumbar spine support including a posterior shell form-fitted around the corresponding torso area. This shell is connectable by a flexible strap arrangement tightly against the torso. The posterior shell includes an elongated upright indentation having a laterally extending wider lower portion for centering and securing the posterior shell over the lumbosacral area of the spine. A tightening strap arrangement connected to the support belt provides independent right and left side secondary means for increasing tightness of the posterior shell against the torso.

It is therefore an object of this invention to provide an improved lumbar spine support which combines the biomechanical advantages of an asymmetrical shell support with the comfort and convenience of a two-stage and fully adjustable closure system.

It is yet another object of this invention to provide a lumbar spine support which causes hydrostatic lift to occur in the abdominal cavity to relieve the pressure on and to allow equalization of, the discs of the spine.

It is yet another object of this invention to provide a lumbar spine support which, by hydrostatic lift, overcomes the forces of gravity and resists reversing chiropractic adjustments caused by twisting, turning or poor ergonomics.

It is yet another object of this invention to provide a lumbar spine support which is firmly self-positioning on the ASIS, the iliac crest, and the lumbosacral spine to control lumbosacral rotation, thus lessening the possibility of reinjury during healing.

It is yet another object of this invention to provide a lumbar spine support which will adequately support the spine while permitting exercising of the underlying musculature and is of an ultra thin construction to facilitate undergarment wear.

In accordance with these and other objects which will become apparent hereinafter, the instant invention will now be described with reference to the accompanying drawings.

DETAILED DESCRIPTION OF THE INVENTION

Figure 1:
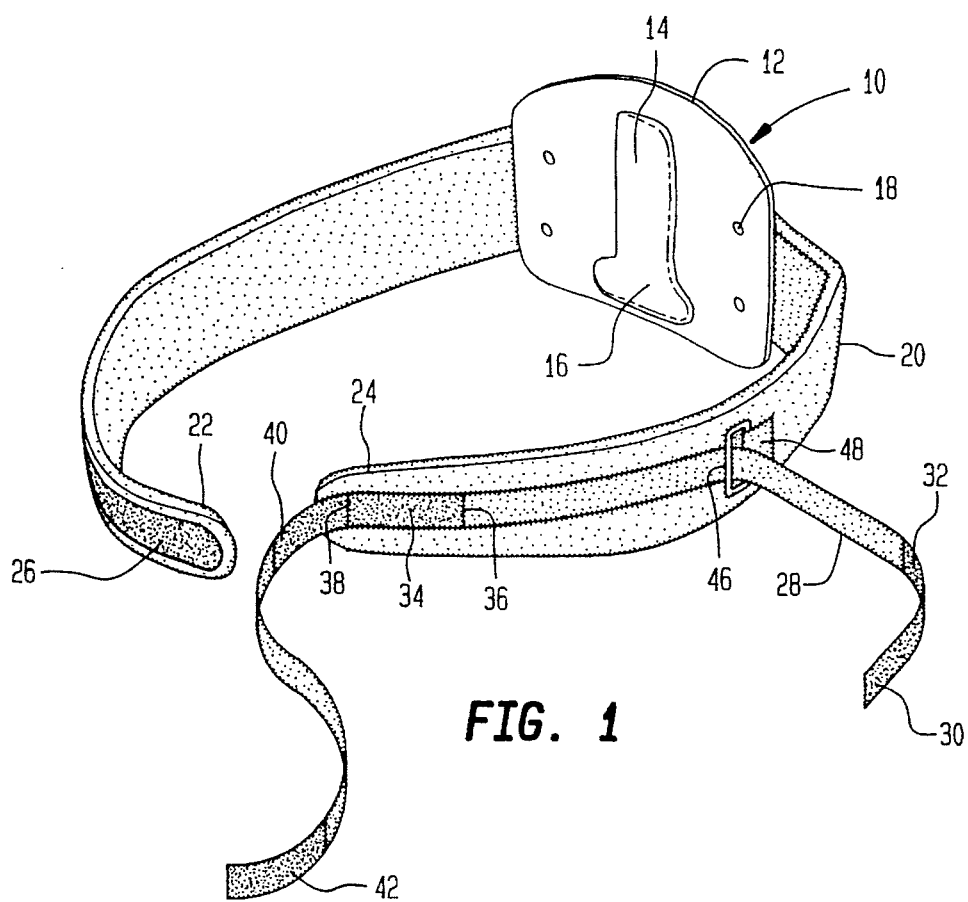
FIG. 1 is a right side perspective view of the invention.
Figure 2:
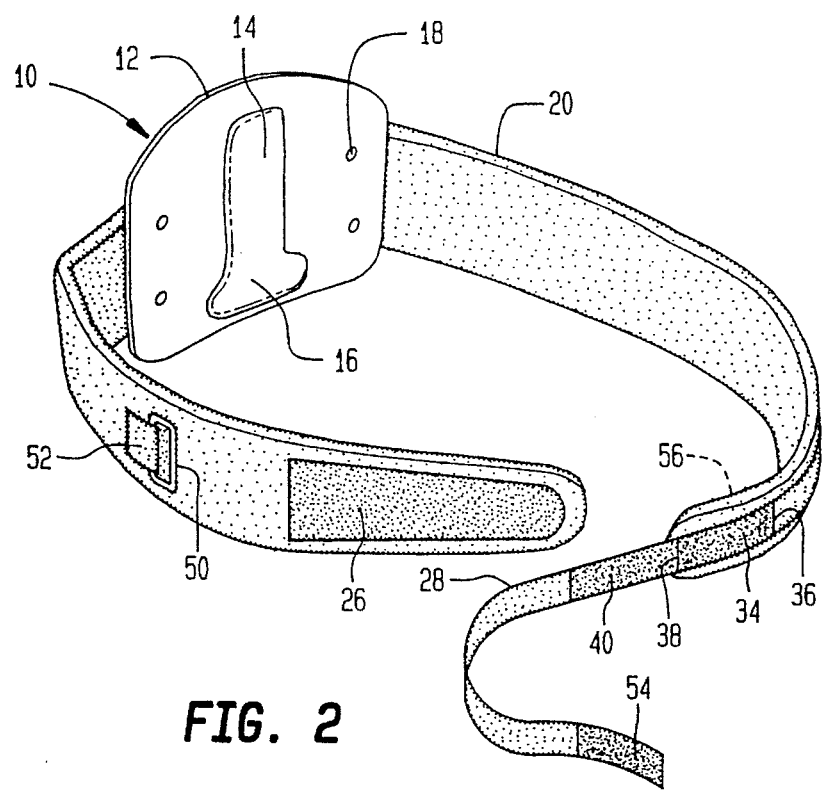
FIG. 2 is a left side perspective view of the invention.

Referring now to the drawings, the invention is shown generally at numeral 10 in all figures and includes a posterior shell 12 which is fabricated of a contour-molded sheet of thermo-plastic material forming an outer layer thereof adhered to an inner layer of compressible, closed cell foam forming an interior surface thereof. This posterior shell 12 is semi-rigid in that some flexure is possible to improve fit and comfort during normal body movement.

The posterior shell 12 includes an elongated, upright indentation 14 formed inwardly into the thermal plastic outer layer of shell 12, the adhered closed cell foam inner layer conforming thereto. This indentation 14 includes a lower elongated transverse portion 16, the combination structured, when posterior shell 12 is positioned as shown in FIG. 4, to guide the placement of the posterior shell 12 for proper centering over the spine and to lock onto the lumbosacral area of the spine for even dispersion of the resilient force when tightly strapped against the posterior torso of the patient.

Figure 4:
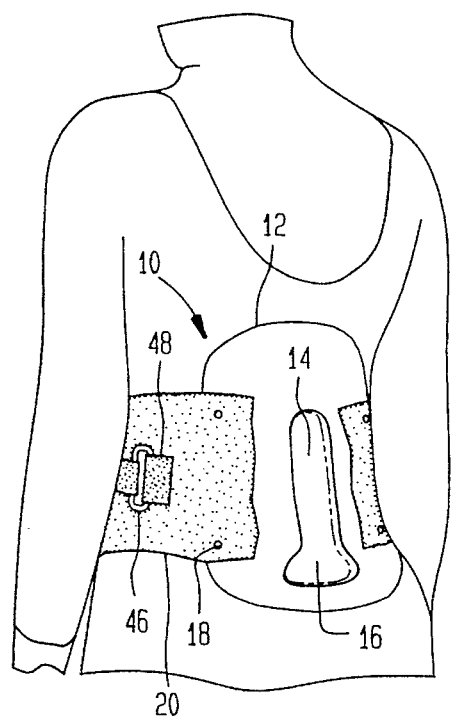
FIG. 4 is a perspective view of the invention in use as viewed from the rear of a user.

After the posterior shell 12 is initially positioned against the posterior torso area as shown in FIG. 4, free ends of a flexible fabric support belt 20, riveted at 18 (typ.) to adjacent lateral upright edges of the posterior shell 12, are drawn forwardly and around the lower abdominal area of the front of the torso so as to overlap one another and to be so held by hook and loop material 26 and 56. A loop or ring 46 and 50 is secured by stitched in place fabric 48 and 52, respectively, adjacent to the posterior shell 12. A flexible tightening strap 28, is secured at a mid region 34 thereof by stitching 36 and 38 against an end portion 24 of the outer surface of support belt 20. One end of the tightening strap 28 is fed through loop 46 back along, and secured against itself at 36 by a releasable attaching means such as hook and loop (VELCRO) arrangement 32/34.

The other end 54 of the tightening strap 28 extends around the left side of the torso and support belt end portion 26 to be feed through and interengage with loop or ring 50 and then be drawn back forwardly around the left side of the torso to be engaged against itself at 40/42.

Figure 3:
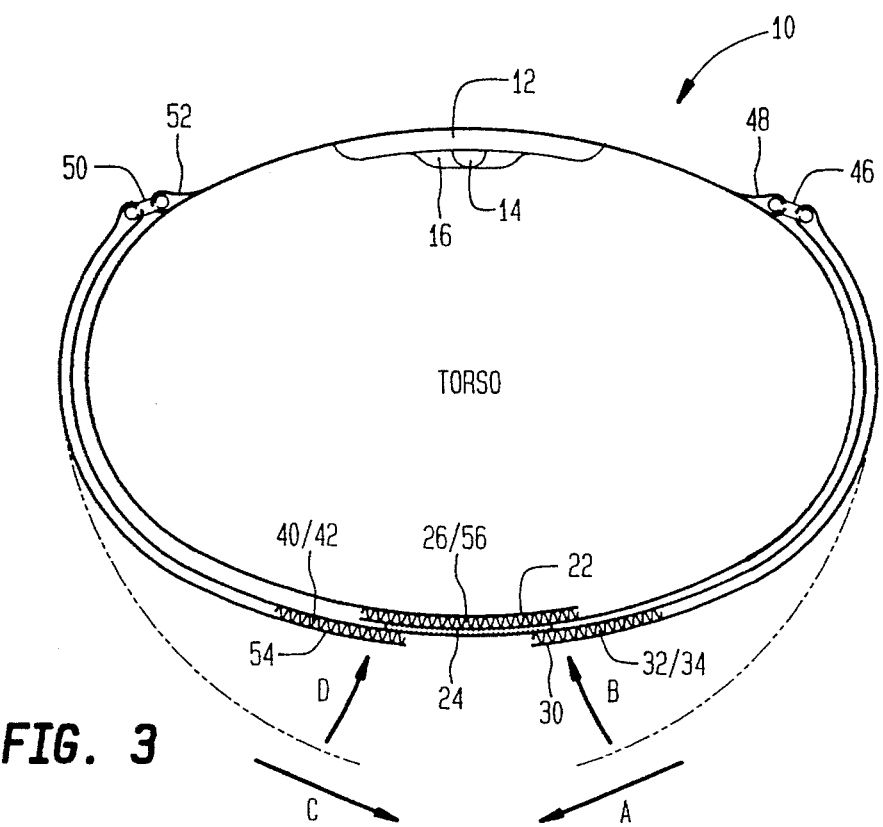
FIG. 3 is a top plan schematic view of the invention in position around a user's torso.

Thus, the distal ends of support belt 20 are first overlapped and tightened and releasably secured together by hook and loop surfaces 26/56 against the lower abdominal area of the torso as seen in FIG. 3 to secure a desired tensioning. To further increase tensioning, the distal ends 30 and 56 of tightening strap 28 are first pulled in the direction of arrows A and C, respectively, either simultaneously or separately. When the desired increased tension is achieved, each end 30 and 54 is moved in the direction of arrows B and D, respectively, for releasable attachment back on itself by hook and loop surfaces 32/34 and 40/42. By appropriate two-stage tensioning of the arrangement in this manner, the upright indentation 14 of posterior shell 12 serves to center and align the entire arrangement so as to properly stabilize the lower spine area from excessive movement.

While the instant invention has been shown and described herein in what are conceived to be the most practical and preferred embodiments, it is recognized that departures may be made therefrom within the scope of the invention, which is therefore not to be limited to the details disclosed herein, but is to be afforded the full scope of the claims so as to embrace any and all equivalent apparatus and articles.

What is claimed is:

1. A lumbar spine support comprising:

a substantially rigid, body contoured, continuous posterior shell having right and left lateral edges which terminate in the right and left posterolateral regions, respectively, of a torso of a patient;

right and left support belt means extending forwardly around the torso from said right and left lateral edges of said posterior shell for providing a first stage of adjustably tightening said posterior shell against the torso;

tightening strap means connected to said right and left support belt means for providing a second stage for independently increasing tightness of said right and left support belt means after engagement of said right and left support belt means.

2. A lumbar spine support as set forth in claim 1, wherein:

said posterior shell including an elongated central upright indentation extending inwardly from the continuous surface of said shell having a laterally extending portion at the lower end thereof and positioned and structured to center and secure said posterior shell over the lumbosacral area of the spine wherein said indentation provides an even dispersion of a resilient force.

3. A lumbar spine support as set forth in claim 2, wherein:

said posterior shell is formed of an outer sheet of thermoplastic connected to an inner layer of closed cell foam.

4. A lumbar spine support as set forth in claim 2, wherein:

said upright indentation is structured, in cooperation with said posterior shell, to conform to the skeletal cavity created at the junction of the lumbar vertebra and the sacrum.

5. A lumbar spine support comprising:

a substantially rigid, body contoured, continuous posterior shell having right and left lateral edges which terminate in the right and left posterolateral regions, respectively, of a torso of a patient;

a flexible supporting belt connected to said posterior shell and extending forwardly from said right and left lateral edges of said posterior shell around the torso;

a right and left end of said supporting belt overlapping and connectable against one another for providing a first stage of adjustably tightening said posterior shell against the torso;

a flexible tightening strap connected at a mid region thereof adjacent to one said end of said supporting belt and extending in either direction along said supporting belt;

a pull ring connected to said supporting belt adjacent each said right and left lateral edges of said posterior shell;

said tightening strap sized in length for each end thereof to pass through one said pull ring, each said tightening strap end doubling back for releasible connection against itself;

said tightening strap providing a second stage for increasably tightening said posterior shell against the torso.

6. A lumbar spine support as set forth in claim 5, wherein:

said posterior shell including an elongated central upright indentation extending inwardly from the continuous surface of said shell having a laterally extending portion at the lower end thereof and positioned and structured to center and secure said posterior shell over the lumbosacral area of the spine wherein said indentation provides even dispersion of a resilient force;

said upright indentation structured, in cooperation with said posterior shell, to conform to the skeletal cavity created at the junction of the lumbar vertebra and the sacrum.

7. A lumbar spine support as set forth in claim 6, wherein:

said posterior shell is formed of an outer sheet of thermoplastic adhered to and coextensive with an inner layer of closed cell foam.

* * * * *